(12) United States Patent
Stone et al.

(10) Patent No.: US 7,338,528 B2
(45) Date of Patent: Mar. 4, 2008

(54) HUMERAL STEM WITH ANATOMICAL LOCATION OF TAPER ACCESS FOR FIXATION OF HUMERAL HEAD

(75) Inventors: Kevin T. Stone, Winona Lake, IN (US); Nicholas M. Cordaro, Cardiff by the Sea, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 10/358,079

(22) Filed: Feb. 4, 2003

(65) Prior Publication Data

US 2004/0153161 A1   Aug. 5, 2004

(51) Int. Cl.
*A61F 2/40* (2006.01)
(52) U.S. Cl. .................................. 623/19.14
(58) Field of Classification Search ............ 623/11.11, 623/16.11, 18.11, 19.11–19.14
See application file for complete search history.

(56) References Cited

U.S. PATENT DOCUMENTS

| | | | |
|---|---|---|---|
| 3,842,442 A * | 10/1974 | Kolbel | 623/19.12 |
| 5,314,479 A | 5/1994 | Rockwood, Jr. et al. | |
| 5,358,526 A | 10/1994 | Tornier | |
| 5,489,309 A * | 2/1996 | Lackey et al. | 623/19.14 |
| 5,549,682 A | 8/1996 | Roy | |
| 5,702,486 A * | 12/1997 | Craig et al. | 623/19.14 |
| 5,910,171 A | 6/1999 | Kummer et al. | |
| 6,102,953 A * | 8/2000 | Huebner | 623/19.11 |
| 6,120,542 A * | 9/2000 | Camino et al. | 623/19.11 |
| 6,197,062 B1 * | 3/2001 | Fenlin | 623/19.12 |
| 6,197,063 B1 | 3/2001 | Dews | |
| 6,206,925 B1 * | 3/2001 | Tornier | 623/19.12 |
| 6,228,120 B1 * | 5/2001 | Leonard et al. | 623/19.12 |
| 6,283,999 B1 * | 9/2001 | Rockwood, Jr. | 623/19.12 |
| 6,494,913 B1 * | 12/2002 | Huebner | 623/19.11 |
| 6,508,840 B1 * | 1/2003 | Rockwood et al. | 623/19.12 |
| 6,676,705 B1 * | 1/2004 | Wolf | 623/19.14 |
| 6,736,851 B2 * | 5/2004 | Maroney et al. | 623/19.12 |
| 6,776,799 B2 * | 8/2004 | Ball et al. | 623/19.11 |
| 7,011,686 B2 * | 3/2006 | Ball et al. | 623/19.14 |
| 2001/0041940 A1 | 11/2001 | Pearl | |
| 2001/0049561 A1 | 12/2001 | Dews et al. | |
| 2001/0053935 A1 | 12/2001 | Hartdegen et al. | |
| 2003/0028253 A1 * | 2/2003 | Stone et al. | 623/19.14 |

* cited by examiner

*Primary Examiner*—Anuradha Ramana
(74) *Attorney, Agent, or Firm*—Harness, Dickey & Pierce, P.L.C.

(57) ABSTRACT

Disclosed is a kit having a set of humeral components used in partial and total joint replacement surgeries. The set of humeral components has a plurality of stems having varying stem diameters and a set of humeral heads having hemispheric surfaces with varying radiuses. Each stem defines a platform having a hole which is a fixed distance from the proximal end of the stem. The distance of the hole from the proximal end of the stem is a function of the stem diameter.

10 Claims, 5 Drawing Sheets

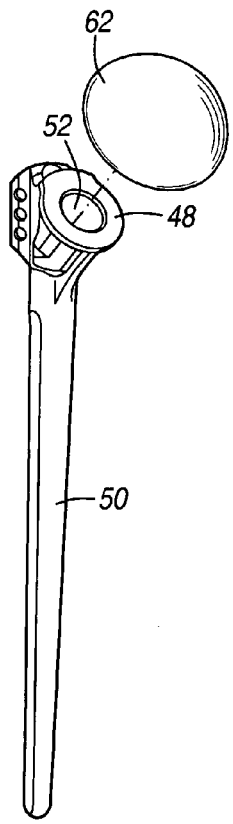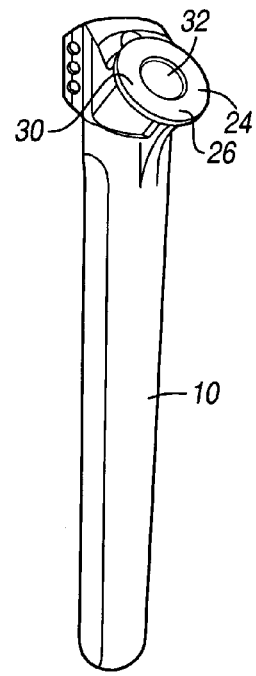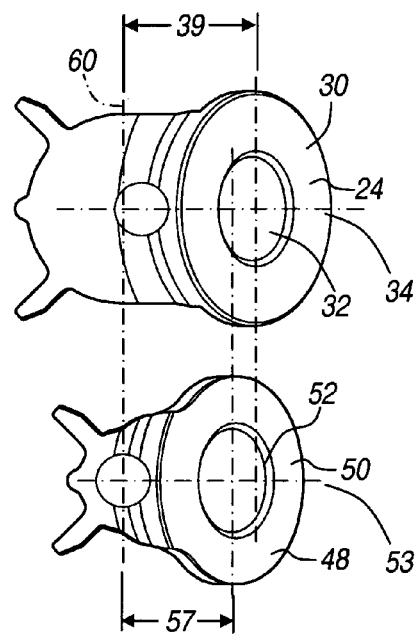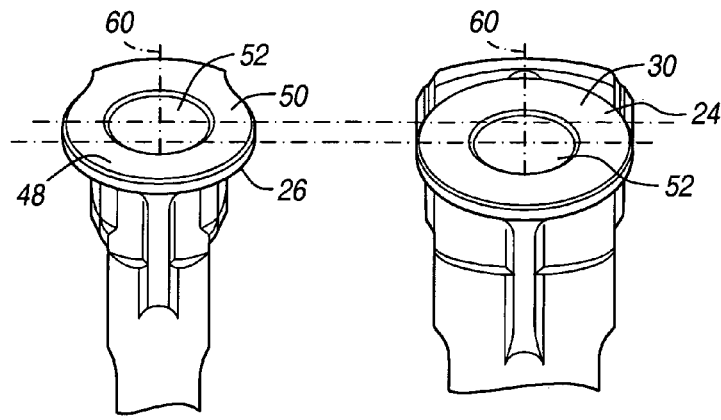
FIG. 3  FIG. 4  FIG. 5
FIG. 6

HUMERAL STEM WITH ANATOMICAL LOCATION OF TAPER ACCESS FOR FIXATION OF HUMERAL HEAD

BACKGROUND OF THE INVENTION

1. Field of the Invention

This invention relates generally to an apparatus and method for shoulder arthroplasty and, more particularly, to a humeral component and other associated surgical components and instruments for use in shoulder arthroplasty.

2. Discussion of the Related Art

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus is resected and a cavity is created in the intramedullary canal of the host humerus for accepting a humeral component. The humeral component includes a head portion used to replace the natural head of the humerus. Once the humeral stem component has been implanted, the humeral head is sized and positioned at the scapula head to ensure proper movement. The glenoid may also be resurfaced and shaped to accept a glenoid component. The glenoid component generally includes an articulating surface which is engaged by the head portion of the humeral component.

It is generally known in the art to provide a shoulder joint prosthesis having a humeral component, as discussed above. However, the current prior art humeral components along with the associated surgical components and instruments utilized during shoulder arthroplasty suffer from many disadvantages.

For example, since the humeral component is subject to various types of loading by the surface of the glenoid component, the humeral component must offer a stable and secure articulating surface. To achieve this, the humeral components provide stems which are inserted into a hole bored into the intermedullary canal. However, such existing stemmed humeral components also exhibit several disadvantages. For example, some of the stemmed humeral components utilize single centered stems of various sizes to stabilize and secure the humeral component to the humerus. While the hemispherical radius of the head can be adjusted to compensate for differences in the stem size, use of such an adjusted head radius does not always provide proper spacing and allow proper joint articulation since the articulation axis of the head does not change with the change in head size. To overcome this, a myriad of designs offer heads having offset pegs and sleeves, thus increasing the complexity of the surgery. Furthermore, the offset head designs require heads having varying hemispherical shape in conjunction with the sleeves to allow for a proper joint functioning.

As shown in FIGS. 1a and 1b, most prior art humeral components rely on stems 100 having a single fixed offset from the proximal end of the stem. The heads 102 to be coupled to the stems 100 are situated so that the articulating surfaces 104 and 104' are parallel. In instances where the head 102 has a large diameter, a portion of the head 102 overlaps the longitudinal axis a significant amount. This is an undesirable condition which leads to improper joint kinematics. The stems 100 may also include extensions which act to anchor the stem within the intermedullary canal once the stem is cemented within the humerus. The proximal end of most humeral components are, thus, generally overlooked to enhance the articulation and are, therefore, generally standardized.

What is needed then is a humeral component and associated surgical components for use in a shoulder arthroplasty which does not suffer from the above-mentioned disadvantages. This in turn, will provide a humeral component which is stable and secure, reduces the overall amount of bone tissue required to be removed, reduces the overall surgical time and complexity, increases overall joint articulation, and enhances and increases natural articulation without increasing overall component count. It is, therefore, an object of the present invention to provide such a humeral component and associated surgical components for use in shoulder arthroplasty.

SUMMARY OF THE INVENTION

In accordance with the teachings of the present invention, an apparatus and method for shoulder arthroplasty is disclosed. The apparatus and method employ a humeral component and other associated surgical components for use in shoulder arthroplasty. In this regard, the humeral component is adapted to be implanted into the humerus within the intermedullary cavity and engaged by the bearing surface of a glenoid component.

The present invention discloses a kit having a set of humeral components. The set of humeral components has a plurality of stems having varying stem diameters and a set of humeral heads having hemispheric surfaces with varying radiuses. Each stem defines a platform having a hole which is a fixed distance from the proximal end of the stem. The distance of the hole from the proximal end of the stem is a function of the stem diameter.

In a further embodiment, the implant includes an articulating head having a first hemispherical radius paired with a first stem. The kit further has a second articulating head having a second hemispherical radius paired with a second stem. Each stem defines a stem center line. The articulating heads are mateable to the stems so that the heads overlap the center line less than a predetermined amount.

A further embodiment to the invention is directed toward a modular prosthesis for implant into a humerus of a patient including a proximal head coupling device. The proximal head coupling device is configured to accept heads having an articulating surface. The head is coupled to the proximal head coupling device such that the articulating surface is offset a predetermined distance from a feature of the proximal head coupling device.

The present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 3 and 4 represent exploded perspective views of the humeral prosthetic shown in FIG. 2;

FIGS. 5 and 6 represent views of the coupling portion of the prosthetic shown in FIGS. 3 and 4;

Figures 1A, 1B:
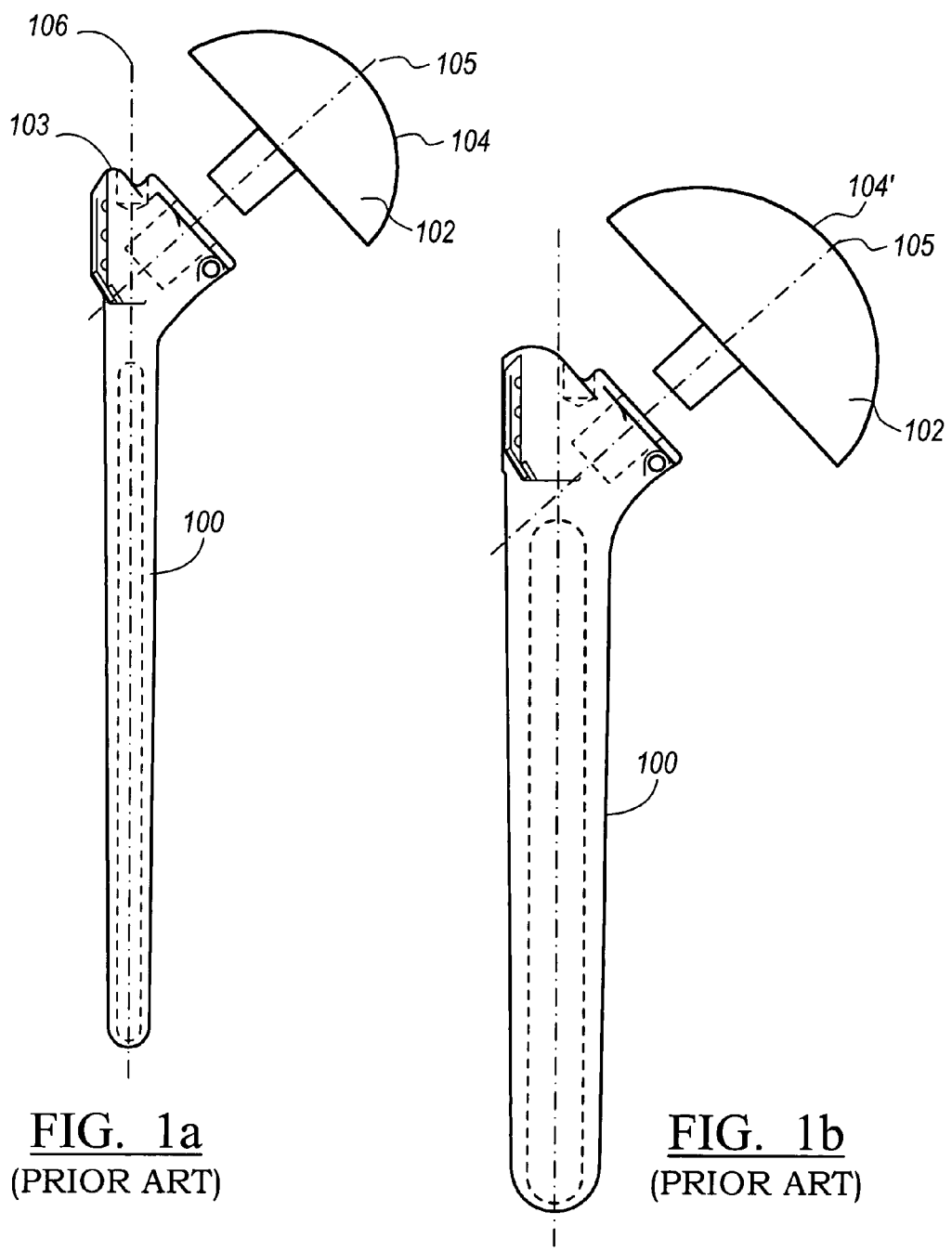
FIGS. 1a and 1b represent a prior art humeral system.
Figures 2A, 2B:
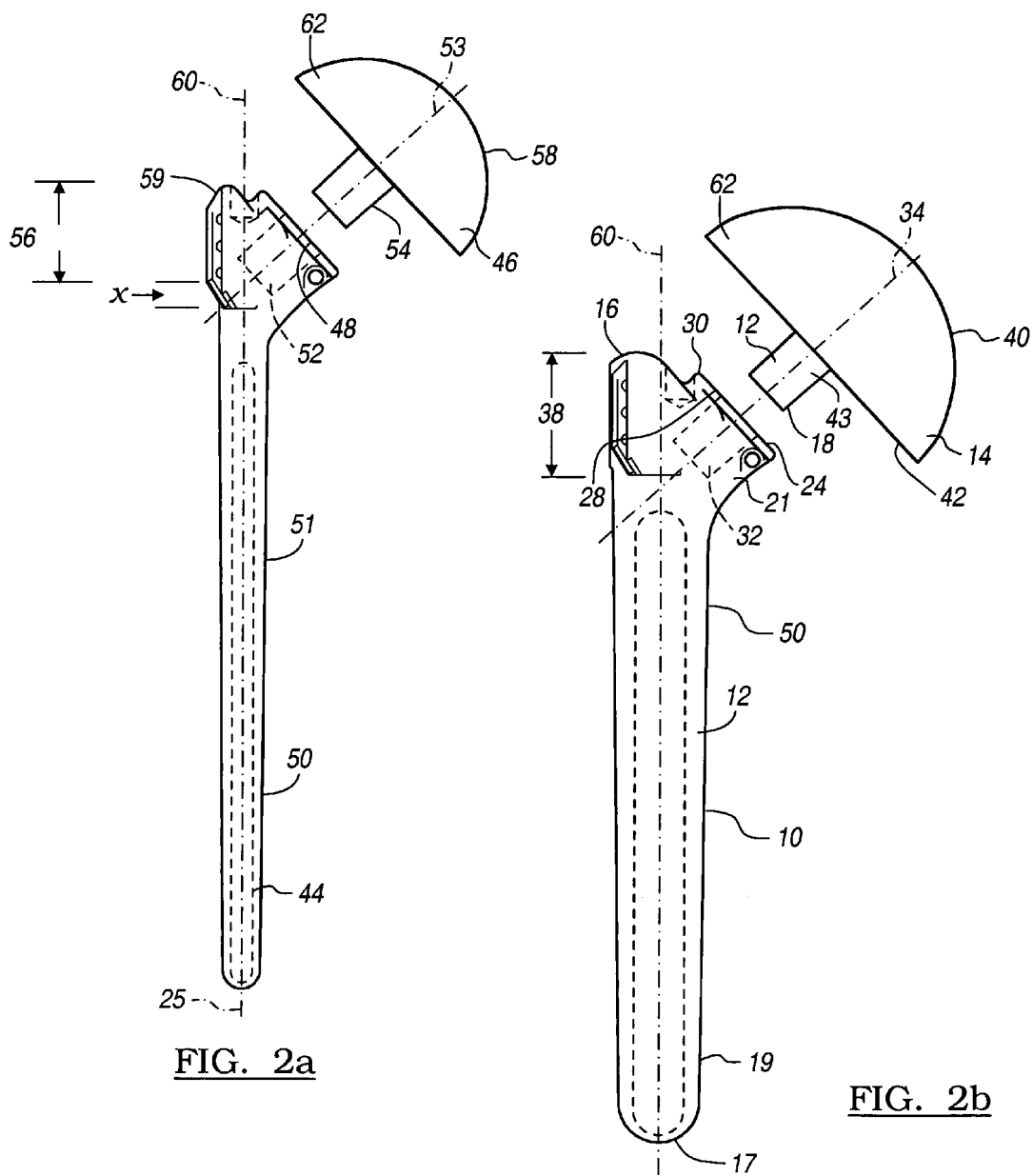
FIGS. 2a and 2b represent two humeral prosthetics according to the teachings of the present invention with one shown in phantom.

The description of the invention is merely exemplary in nature and, thus, variations that do not depart from the gist of the invention are intended to be within the scope of the invention. Such variations are not to be regarded as a departure from the spirit and scope of the invention.

DETAILED DESCRIPTION OF THE PREFERRED EMBODIMENTS

The following description of the preferred embodiments concerning an apparatus and method for shoulder arthroplasty is merely exemplary in nature and is in no way intended to limit the invention, its application, or uses. Moreover, while the present invention is directed to a shoulder joint, the present invention may be employed in other joints as well, such as a hip joint.

With reference to FIGS. 2a-4 represent a kit which contains a pair of modular humeral prosthesis 10 and 50 are shown. Referring now to the first prosthesis 10, which has a stem portion 12, and humeral head 14. When assembled, the humeral head 14 is joined to the stem 12 by means of a Morse Taper 18. Components of the Morse Taper 18 are formed on the stem 12 and the head 14. Disposed between a proximal end 16 and a distal end 17 of the stem 12 is a tapered shaft 19 having a first cross-sectional diameter. Disposed on the proximal end 16 of the stem portion 12 is a coupling portion 21 having a platform 24.

The platform 24 has a lower surface 26 which mates with the resected bone surface 28 as shown in FIG. 2. The platform 24 further has an annular upper surface 30 which mates with the head 14. Defined within the platform 24 is the female portion 32 of Morse Taper 18. The female portion 32 has an axis 34 that is generally perpendicular to the upper surface 30 of the platform 24. Further, the axis 34 is defined having a fixed distance 38 to the proximal end 16 of the stem portion 12. The fixed distance 38 is a function of one of the average cross sectional diameter or cross-sectional area of the tapered shaft 19.

Shown disposed above the shaft 12 is a humeral head 14. The humeral head 14 defines a hemispherical articulating surface 40 and a planar coupling surface 42. The coupling surface 42 functions to couple to the upper surface 30 of the platform 24. Defined in the coupling surface 42 is the male portion 43 of the Morse Taper 18. It is envisioned that either the stem or the head can have either the male or female side of the Morse Taper. Furthermore, other fixation methods such as threaded members can be incorporated. The hole disposed in the stem 12 is threaded to rotatably receive a threaded head portion. The hemispherical surface 40 functions to rotatably mount to the glenoid (not shown).

The head component 14 can be comprised of any number of biocompatible materials, such as but not limited to titanium, cobalt chrome, stainless steel, ceramics or any other material that can serve as a bearing surface. The head component 14 can articulate either on the natural glenoid or on a glenoid component (not shown) such as one made of cobalt chrome or any other suitable biocompatible material in order to provide for a metal-metal articulation.

The head component 14 is shown as being substantially hemispherical in shape, although the present invention envisions modifications to the shape shown. For example, the head component 14 can be either a full, greater than full, or partial hemisphere.

Anatomical differences between patients dictate the proper diameter of the stem 12 be used to properly mate the stem within the intermedullary canal of the humerus. These anatomical differences further dictate the radius of curvature of the hemispherical surface 40.

Reference is now made to the second prosthesis 50 in FIG. 2, which represents a second humeral prosthesis 50 according to the teachings of the present invention. Shown is a second stem portion 44 and second head portion 46. The second stem portion 44 is defined by a second tapered shaft 51. Further, the stem has a platform 48 defining a head mating surface 50. Again defined within the head mating surface is the female portion 52 of the Morse Taper 54. The axis 53 of the Morse Taper 52 is defined at a second fixed distance 56 of the proximal end 58 of second prosthesis 50. Further, the axis 34 of the Morse Taper 52 is substantially parallel to the axis 39 for the first prosthetic 10. The fixed distance 56 is a function of the average diameter or the cross sectional area of the stem.

Further shown is the second head portion 46 which has a hemispherical surface 59. The hemispherical surface 59 has a radius smaller than the radius of the first humeral head 14.

The humeral prostheses 10 and 50 shown in FIG. 2 are depicted sharing a common center line 60 which corresponds to the center line of the intramedullary canal to which the prostheses are being implanted. As can be seen, the center lines of the axis 34 and 53 are displaced from each other a predetermined distance x and intersect the longitudinal axis 60. The distance x is a function of the difference of the average tapered stem diameters or cross sectional area of stems 19 and 44.

As can further be seen, each head 14 and 46 have a lateral side 62 which are less than 2 millimeters and preferably less than 2 millimeters in the lateral side from the common center line or longitudinal axis 60 of the humeral prostheses 10 and 50. This is opposed to the distance from the center line of the prior art systems (see FIG. 1) which overlap the center line more than 2 mm. Furthermore, by adjusting the location of the axis 34 for a large headed implant, the radius of curvature will change to provide a better angle of curvature with respect to the inferior side of the glenoid.

FIGS. 3 and 4 represent an exploded perspective view of the humeral prosthesis 10 and 50 shown in FIG. 2. FIG. 3 represents a prosthetic having a 6 millimeter diameter stem, while FIG. 4 represents a prosthetic having a 15 millimeter diameter stem. Shown also are the upper surfaces 30 and 56, which are planar. It is envisioned that these surfaces can take any shape such as convex or concave.

The stem components 10 and 50 can be configured in any number of shapes (e.g., curved, tapered, conical, cylindrical, radial, fluted, and so forth). The surface finish of the stem components 10 and 50 can be smooth, plasma spray, porous coating, threaded, polished, grit blasted, and so forth). The material comprising the stem components 10 and 50 can be any biocompatible material such as but not limited to titanium, cobalt chrome, stainless steel, ceramics, and so forth.

The cross-sectional profile of the stem component 12 may comprise many different shapes, and can either be used in a press-fit or cemented application for implantation.

FIGS. 5 and 6 best depict the humeral head coupling platforms 24 and 48. Depicted is the relationship of the coupling member axes 25 and 53 with respect to the humeral prosthetic center lines 60. In this regard, the coupling mechanism is a first distance along the longitudinal axis from the first proximal end, while the second coupling mechanism is a second distance from the second proximal end. Shown in these views is the clear offset of the axes 25 and 53 from the proximal ends 22 of the stem portions. The difference in fixed distance can also be measured at any fixed point along the stems.

Figure 7:
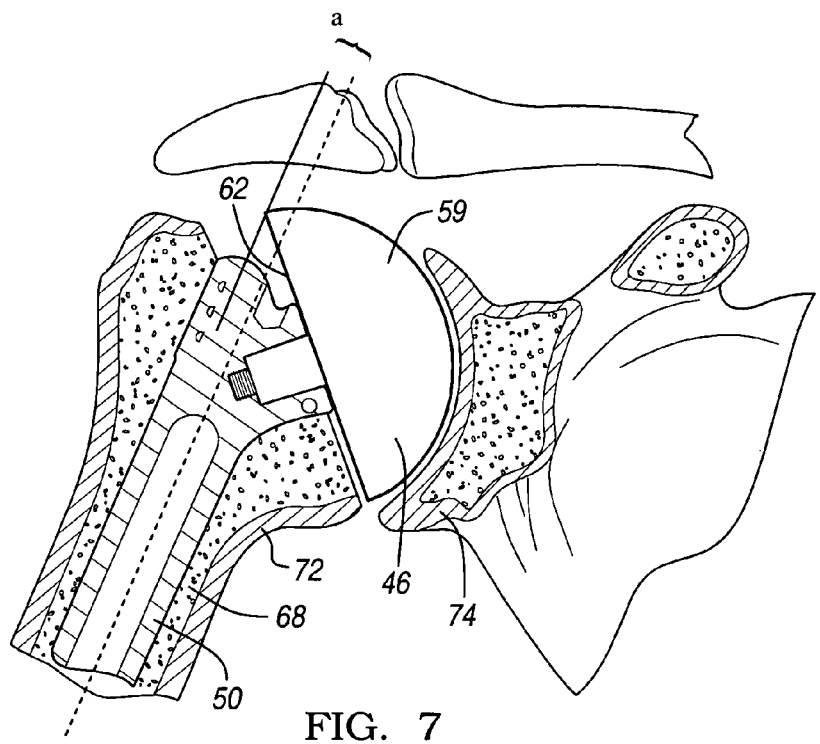
FIG. 7 is a cross sectional view of the prosthetic according to FIG. 3 shown implanted in a shoulder.
Figure 8:
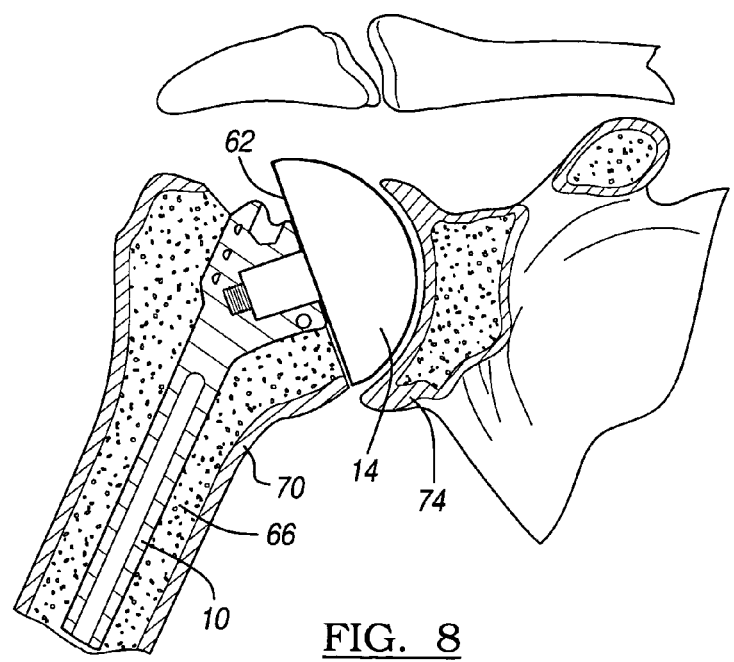
FIG. 8 is a cross sectional view of the prosthetic according to FIG. 4 shown implanted in a shoulder.

FIGS. 7 and 8 represent implanted humeral prostheses 10 and 50. Shown are the prosthesis 10 and 50 disposed within the intermedullary canal 66 and 68 of the resected humerus 70 and 72. In each case, the coupled head portions 14 and 46 are shown in articulating contact with a natural glenoid 74. It is envisioned that the current system can be used with an artificial glenoid in a total joint replacement.

By having the lateral side 62 of the head portions 14 and 46 overlap the common center line 60 (see a) by less than 5 millimeters and more preferably less than 2 millimeters, proper joint articulation can be achieved using no adaptive intermediate components between the head and stems. This significantly reduces the complexity of the prosthesis as well as improves the prosthetic life expectancy and for liability.

Figures 9, 10:
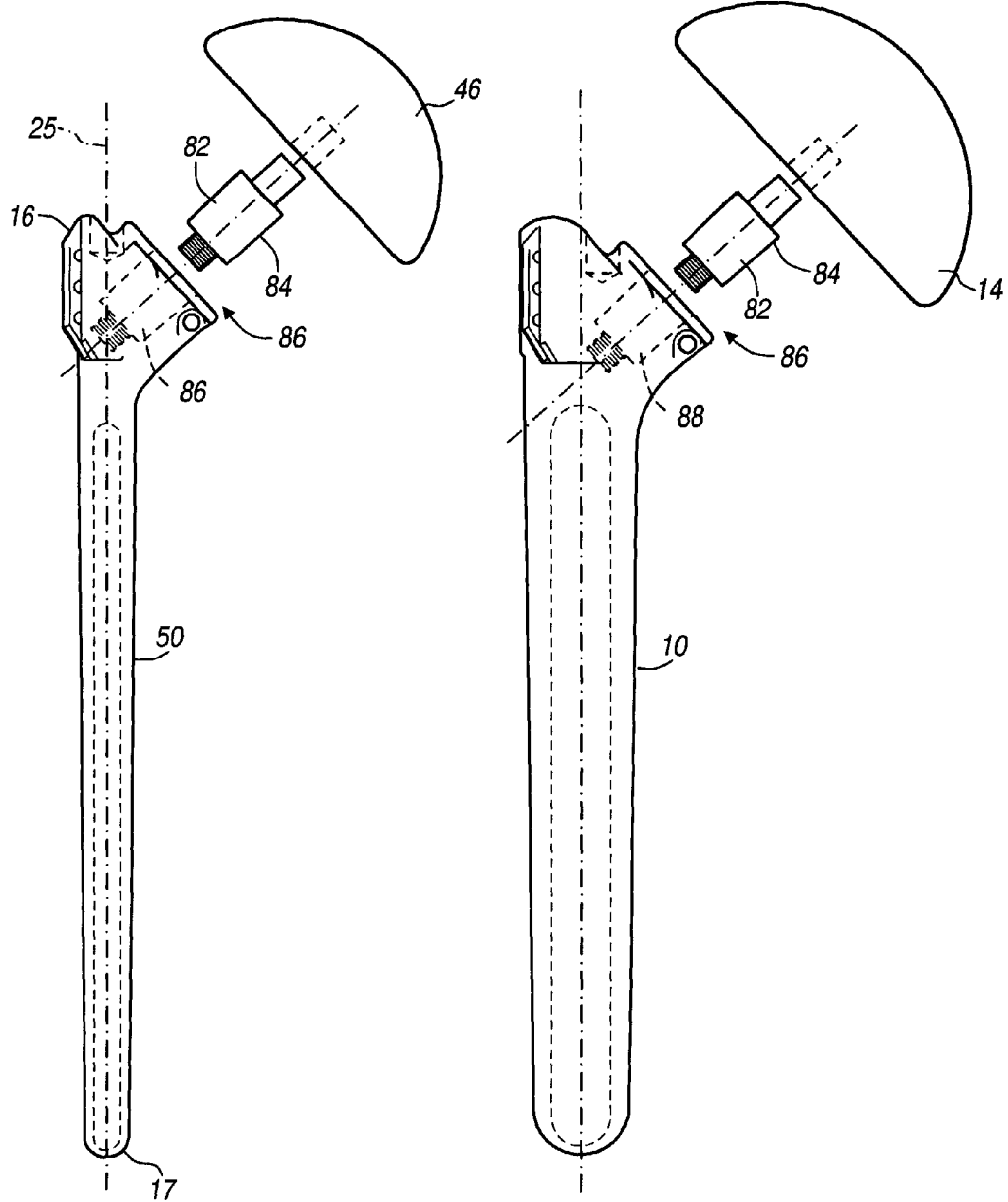
FIGS. 9 and 10 represent side views of an alternate embodiment of the present invention.

FIGS. 9 and 10 represent an alternate method for coupling the head portions 14 and 46 to the stem portions 10 and 50. Shown is an intermediary member 82 which is coupled to the stem by way of a threaded post 84 further defined on the intermediary member 82 is the male side 84 of a Morse Taper 86. The male side 84 is coupled to the female portion 88 of the Morse Taper 86 defined in the head portions 14 and 46.

The humeral prosthesis 10 is shown with stem 12 having longitudinal axis 25, and proximal and distal ends 16. The hemispherical head 14 can be coupled to the proximal end having an apparent diameter of greater than about 51 mm where apparent diameter is the intersection of the head within the centerline. The hemispherical head 14 overlaps the longitudinal axis 25 in the lateral direction less than about 5 mm and preferably less than 2 mm, when the distal end 17 of the stem 12 is extending in the inferior position.

Further, the humeral components 10 and 50 can have a diameter greater than about 43 mm; wherein said hemispherical head overlaps the longitudinal axis 25 in the lateral direction less than 5 mm and preferably less than 2 mm when the distal end 17 of the stem 12 is extending in the inferior position.

The foregoing discussion discloses and describes merely exemplary embodiments of the present invention. One skilled in the art will readily recognize from such discussion and from the accompanying drawings and claims that various changes, modifications, and variations can be made therein without departing from the spirit and scope of the invention.

What is claimed is:

1. A kit of prosthetic components comprising:
    a first monolithic stem having a first longitudinal axis and a first proximal end defining a first mounting portion, said first mounting portion defining a first coupling mechanism having a first taper having a first coupling mechanism axis, said coupling mechanism axis intersecting the first longitudinal axis at a first fixed distance along the first longitudinal axis from said first proximal end wherein the first proximal end and mounting portion are a monolithic structure; and
    a second monolithic stem having a second longitudinal axis and a second proximal end defining a second mounting portion, said second mounting portion defining a second coupling mechanism with a second taper having a second coupling mechanism axis, said second coupling mechanism axis intersecting the second longitudinal axis at a second fixed distance along the second longitudinal axis from said second proximal end wherein the second proximal end and mounting portion are a monolithic structure and said first distance is less than said second distance, and a first head selectively mateable with either the first or second coupling mechanisms, the head having a medial edge displaced from the first longitudinal axis of the first monolithic stem or the second longitudinal axis of the second monolithic stem by less than about 5 millimeters.

2. The kit according to claim 1 further comprising a second head capable of being mated to one of the second or first stems.

3. The kit according to claim 2 wherein said head has an articulating surface with a first rim radius.

4. The kit according to claim 3 wherein said second head has an articulating surface with a second rim radius, said second hemispherical radius being larger than said first rim radius.

5. The kit of humeral prostheses which are mateable with a resected humerus comprising:
    a first monolithic stem having a first proximal end and defining a first central line and a mounting portion monolithic with the first proximal end, said mounting portion defining an integral first female Morse taper coupling mechanism, said coupling mechanism having a coupling mechanism axis which intersects the first centerline at a first distance from said proximal end;
    a first head having a first convex articulating surface and being capable of being fixedly coupled to said first stem, said first head having a first medial edge, said medial edge overlapping the first centerline by less than about 5 millimeters when said first stem and first head are mated;
    a second monolithic stem having a second proximal end defining a second center line and a second mounting portion monolithic with the second proximal end, said second mounting portion defining an integral second female Morse taper coupling mechanism, said second coupling mechanism having a second coupling mechanism axis which intersects the second centerline at a second distance from said second proximal end; and
    a second head having a second convex articulating surface, said second head being capable of being fixedly coupled to said second stem, said second head having a second medial edge, said second medial edge overlapping said second centerline by less than 5 millimeters when said second stem and second head are mated, wherein said first distance is less than said second distance.

6. The kit according to claim 5 wherein said first head has an articulating surface with a first hemispherical radius.

7. The kit according to claim 6 wherein said second head has a second hemispherical radius greater than said first hemispherical radius.

8. The kit according to claim 5 wherein said first head is mateable with said second stem.

9. The kit according to claim 8 wherein said second head is mateable with said first stem.

10. The kit according to claim 5 wherein said first coupling mechanism defines a first coupling member axis, and wherein said second coupling member defines a second coupling member axis, wherein said first coupling member axis and said second coupling member axis are substantially parallel when the first and second center lines are parallel.

* * * * *